(12) United States Patent
Aukrust et al.

(10) Patent No.: US 11,090,276 B2
(45) Date of Patent: Aug. 17, 2021

(54) FORMULATION OF FAT-SOLUBLE VITAMIN

(71) Applicant: BASF SE, Ludwigshafen (DE)

(72) Inventors: Inger Reidun Aukrust, Oslo (NO); Helena M. Larsson, Malmö (SE); Thomas Rove, Vanlose (DK)

(73) Assignee: BASF SE, Ludwigshafen (DE)

( * ) Notice: Subject to any disclaimer, the term of this patent is extended or adjusted under 35 U.S.C. 154(b) by 263 days.

(21) Appl. No.: 15/308,926

(22) PCT Filed: May 5, 2015

(86) PCT No.: PCT/EP2015/059884
§ 371 (c)(1),
(2) Date: Nov. 4, 2016

(87) PCT Pub. No.: WO2015/169816
PCT Pub. Date: Nov. 12, 2015

(65) Prior Publication Data
US 2017/0056339 A1    Mar. 2, 2017

(30) Foreign Application Priority Data

May 5, 2014  (EP) .................................... 14166967

(51) Int. Cl.
| | | |
|---|---|---|
| *A61K 31/122* | (2006.01) | |
| *A61K 45/06* | (2006.01) | |
| *A23P 10/30* | (2016.01) | |
| *A23P 10/35* | (2016.01) | |
| *A23L 33/15* | (2016.01) | |
| *A61K 9/20* | (2006.01) | |
| *A61K 9/16* | (2006.01) | |
| *A61K 9/50* | (2006.01) | |
| *A61K 31/593* | (2006.01) | |
| *A61K 33/08* | (2006.01) | |
| *A61K 33/10* | (2006.01) | |
| *A61K 31/592* | (2006.01) | |
| *A23K 20/174* | (2016.01) | |
| *A23K 20/20* | (2016.01) | |
| *A23L 33/16* | (2016.01) | |
| *A23L 2/52* | (2006.01) | |
| *A61K 9/00* | (2006.01) | |

(52) U.S. Cl.
CPC .......... *A61K 31/122* (2013.01); *A23K 20/174* (2016.05); *A23K 20/20* (2016.05); *A23L 2/52* (2013.01); *A23L 33/15* (2016.08); *A23L 33/16* (2016.08); *A23P 10/30* (2016.08); *A23P 10/35* (2016.08); *A61K 9/0053* (2013.01); *A61K 9/1623* (2013.01); *A61K 9/1652* (2013.01); *A61K 9/2054* (2013.01); *A61K 9/2077* (2013.01); *A61K 9/2081* (2013.01); *A61K 9/2095* (2013.01); *A61K 9/5042* (2013.01); *A61K 31/592* (2013.01); *A61K 31/593* (2013.01); *A61K 33/08* (2013.01); *A61K 33/10* (2013.01); *A61K 45/06* (2013.01); *A23V 2002/00* (2013.01)

(58) Field of Classification Search
CPC ..... A61K 31/122; A23K 20/174; A23L 33/16; A23L 33/15; A23P 10/30
See application file for complete search history.

(56) References Cited

U.S. PATENT DOCUMENTS

| | | | | |
|---|---|---|---|---|
| 2004/0247658 | A1* | 12/2004 | Trubiano | ................... A61P 9/00 424/450 |
| 2011/0014288 | A1* | 1/2011 | Hansen | .................... A61K 9/50 424/484 |

FOREIGN PATENT DOCUMENTS

| | | |
|---|---|---|
| CN | 101401809 A | 4/2009 |
| CN | 101422446 A | 5/2009 |
| CN | 101902922 A | 12/2010 |
| CN | 102318835 A | 1/2012 |
| JP | S63-65945 A | 3/1988 |
| JP | 2006-320311 A | 11/2006 |
| WO | WO-91/06292 A1 | 5/1991 |
| WO | WO-2007/045488 A1 | 4/2007 |
| WO | WO-2009/080702 A1 | 7/2009 |
| WO | WO-2009/095240 A1 | 8/2009 |
| WO | WO-2010/035000 A1 | 4/2010 |
| WO | WO-2013/053793 A1 | 4/2013 |
| WO | WO-2013/128037 A1 | 9/2013 |
| WO | WO-2013/153220 A1 | 10/2013 |
| WO | WO-2014/028621 A1 | 2/2014 |

OTHER PUBLICATIONS https://www.nutraceuticalsworld.com/contents/view_suppliers-corner/2013-11-01/kappa-bioscience-delivers-new-microencapsulated-vitamin-k2/ (Year: 2013).*
International Search Report for PCT/EP2015/059884 dated Jun. 11, 2015.
Saha et al., "Hydrocolloids as thickening and gelling agents in food: a critical review," Journal of Food Science and Technology, vol. 47, No. 6, pp. 587-597, 2010.
Garti, Nissim and Reichman, Dov (1993) "Hydrocolloids as Food Emulsifiers and Stabilizers," *Food Structure*: vol. 12: No. 4, Article 3.
SCCS (Scientific Committee on Consumer Safety), Opinion on vitamin K1 (phytonadione), Mar. 23, 2010.
Jin, Qingzhe, "Functional Lipids," China Light Industry Press, p. 133, Aug. 2013.

* cited by examiner

*Primary Examiner* — Taeyoon Kim
*Assistant Examiner* — Tiffany M Gough
(74) *Attorney, Agent, or Firm* — Faegre Drinker Biddle & Reath LLP

(57) ABSTRACT

The invention relates to a composition comprising A) microcapsules comprising at least one fat-soluble active substance selected from a vitamin K compound or a provitamin or a prodrug of a vitamin K compound embedded in a matrix comprising a hydrocolloid and optionally one or more other matrix components, and B) at least one dietary mineral; as well as uses and products comprising such compositions.

18 Claims, No Drawings

FORMULATION OF FAT-SOLUBLE VITAMIN

RELATED APPLICATIONS

This application is a national stage application (under 35 U.S.C. § 371) of PCT/EP2015/059884, filed May 5, 2015, which claims benefit of European Application No. 14166967.1, filed May 5, 2014.

FIELD OF INVENTION

The present invention relates to new compositions of vitamin K compounds and provitamin and prodrug analogues thereof. These compositions can be used in multimineral products, such as nutraceuticals, e.g. for the fortification of foods or simply in supplements, or can be used in pharmaceuticals for the treatment of a variety of conditions known to benefit from the administration of vitamin K. In particular the invention relates to the microencapsulation and optional further coating of the vitamin or provitamin to enable their use in combination with metal salts which otherwise cause degradation of the vitamin.

BACKGROUND OF THE INVENTION

Vitamin K was discovered around 1935 following studies on the cholesterol metabolism on chicks. Vitamin K denotes a group of lipophilic and hydrophobic vitamins that are needed for the post-translational modification of certain proteins, mostly required for blood coagulation. The protein modification is important for their ability to bind calcium ions, which is necessary for their blood coagulation function. Chemically they are 2-methyl-1,4-naphthoquinone derivatives. Vitamin K is not a single compound; rather it is a series of related homologues. There are two main species Vitamin K1 and Vitamin K2.

Vitamin K1 is also called phylloquinone and has the systematic name all-E-2-methyl-3-(3,7,11,15-tetramethyl-hexadec-2-enyl)naphthalene-1,4-dione. It has the structure:

Vitamin K1:

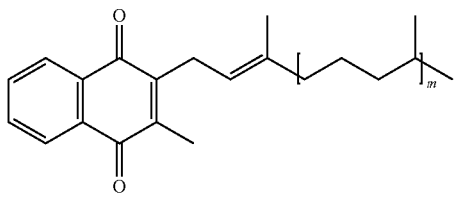

wherein m has the value 3.

Vitamin K2 is a mixture of homologue molecules based on a naphthoquinone structure and varying lengths of the isoprenoid chain. These compounds are called menaquinones. The compound MK-7 comprises 7 isoprenyl groups and is depicted below, but other components of the vitamin have different numbers of isoprenyl groups. Menaquinones have side chains composed of all-E polyprenyl residues; generally they are designated as MK-n, where n specifies the number of isoprenyl repeating units. The minimum value of n is 2 (n typically has a value of 2-11).

Vitamin K2:

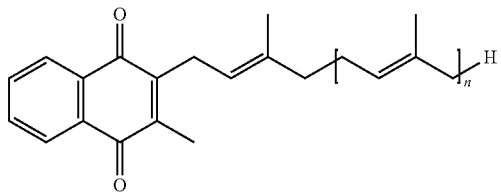

e.g.

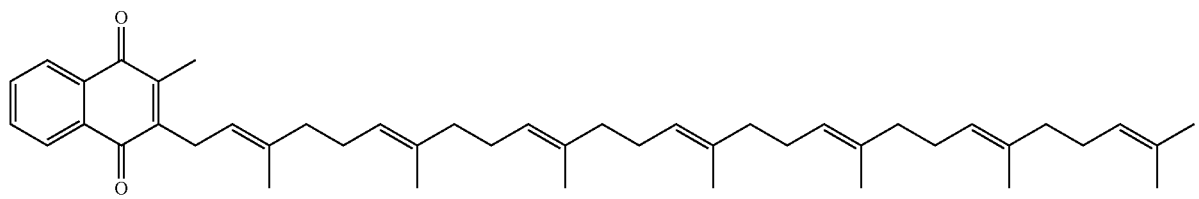 [SMILES: CC(C)=CCC/C(C)=C/CC/C(C)=C/CC/C(C)=C/CC/C(C)=C/CC/C(C)=C/CC/C(C)=C/CC1=C(C)C(=O)c2ccccc2C1=O]

Whilst vitamin K2 occurs naturally in low concentrations in various fermented food products such as cheese and can to a small extent be produced by bacteria in the intestine, its use as a dietary supplement may be beneficial for many populations. Vitamin K2 can be produced by fermentation of soy beans, but it is still an interesting synthetic target as isolation of the vitamin from a natural source is complex and concentrations of the vitamin are low. Moreover, synthesis allows the preparation of particular menaquinones rather than the isolation of a mixture of different menaquinones.

Various individuals have synthesized the menaquinone compounds, which form part of vitamin K2 or components thereof. The first synthesis of menaquinones, reported by Isler et al, Helv Chim Acta (1958) 41, 786-807, used a non-stereospecific approach. Tso and Chen, J Chem Res (1995), 104-105 describes a one pot synthesis of vitamin K although they concentrate on the formation of the naphthoquinone ring as opposed to the side chain of the molecule. The chemistry involves the reaction of 3-substituted isobenzofuranones with vinylic sulphones to form the naphthoquinone ring structure. Suhara et al, Bioorg Med Chem Lett 17, (2007) 1622-1625, describe various syntheses of menaquinone analogues in which the terminal methyl group is converted to a hydroxyl, aldehyde or acid group. Naruta, J Org Chem (1980) 45, 4097-4104, describes the synthesis of some vitamin K2 analogues using trialkylallylstannane chemistry to bond the preformed side-chain to the naphthoquinone group.

A synthetic strategy for the formation of MK-7 and other menaquinones involving the synthesis of a key intermediate in the manufacturing process is disclosed in WO2010/035000. This process enables the formation of large synthetic quantities of vitamin K2 not previously enabled in the prior art. Prodrugs of vitamin K2 are disclosed in WO2013128037.

Vitamin K1 and especially K2 is not stable towards oxygen and light, and conventional preparations containing vitamin K1 and K2 may degrade during processing and storage. Racemisation of the double bonds in the isoprenoid chain leads to inactive vitamin K2 analogues for example, and these double bonds are obviously susceptible to oxidation. Also, the diketone itself of the vitamins is susceptible to oxidation.

It may in particular be desirable to include vitamin K in a multimineral formulation which is a preparation intended for dietary supplement with vitamins, dietary minerals and other nutritional elements. Such preparations are available in the form of tablets, capsules, pastilles, powders, liquids, and injectable formulations and may include e.g. the seven major dietary elements calcium, phosphorus, potassium, sulphur, sodium, chlorine and magnesium and some important minor dietary elements, including iron, cobalt, copper, zinc, molybdenum, iodine and selenium.

However, vitamins K1 and K2 degrade when formulated in a conventional dosage form, such as a tablet, in the presence of mineral salts, in particular calcium or magnesium salts. Moreover, during formulation of the dosage form, there is a still yet further opportunity for degradation. When directly compressed along with some excipients in a tablet such as calcium or magnesium, a serious reduction in the amount of MK-7 present after tableting can be observed, such as up to 30% reduction in MK-7. As MK-7 is expensive, that is not an acceptable loss on formulation. The MK-7 degradation appears to be accelerated in the presence of calcium or magnesium. As calcium and magnesium are valuable minerals, it is desirable to be able to formulate vitamins in general and MK-7 in particular with calcium and magnesium.

The object of the present invention is to provide a new composition comprising a vitamin K product in combination with one or more mineral salts which composition can be formulated in a conventional dosage form such as a tablet without serious degradation of the vitamin during formulation, as well as a process for preparation thereof.

A further object of the invention is to provide a composition which has a desirable high overall stability and good storage properties.

It is a further object of the invention to provide new microcapsules with a content of a vitamin K product which microcapsules when formulated in a conventional dosage form, such as tablets, have good storage properties.

The inventors have realised that a more stable formulation of these vitamins can be prepared using a particular microencapsulation method. By microencapsulating the vitamins before formulation, the overall stability of the vitamin can be markedly improved. Moreover, the resulting powders are easy to handle and stable during processing and have good storage properties over time. During finished product manufacturing it is important that the product has good "flow" properties to minimise losses. The product should be a homogenous blended product, and be resistant to pressure and temperature during the tableting process. After testing and analysis of a large number of potential carriers and coatings, the inventors concluded that only microencapsulation could result in a stable product under the given conditions.

The inventors have also found that microencapsulated vitamin K1 and K2 can be combined with calcium salts, magnesium salts and other metal salts without the degradation issue associated with, for example, MK-7 combined with Ca or Mg directly. The vitamin does not degrade as rapidly as vitamin K1 or K2 during processing and tableting (e.g. direct compression) and the vitamin is more stable to light and air meaning it can be used in applications where light and air exposure are common and has a better storage stability such as in tablets.

The inventors also envisage extending the microencapsulation process to analogues of vitamin K1 and K2, called provitamins or prodrugs herein. The combination of a provitamin/prodrug which converts to the actual vitamin in vivo and the technology described herein therefore forms a further aspect of the invention.

SUMMARY OF THE INVENTION

The present invention relates to a composition comprising:

(A) microcapsules comprising at least one fat-soluble active substance selected from a vitamin K compound or a provitamin or a prodrug of a vitamin K compound embedded in a matrix comprising a hydrocolloid and optionally one or more other matrix components, and (B) at least one dietary mineral.

The invention further relates to a process of preparing a microcapsule for use in the composition of the invention, which process comprises the steps of providing a solution or dispersion of said hydrocolloid and said optionally other matrix components;

adding to said solution or dispersion said at least one fat-soluble active substance, optionally dissolved in a solvent;

treating the mixture thus obtained to prepare a solution or dispersion of said at least one active substance in said matrix;

finely dividing and drying the mixture thus obtained to prepare a mass of particles each containing said at least one active substance embedded in said matrix.

In particular, the invention provides, a process of preparing a microcapsule for use in the composition of the invention, which process comprises the steps of providing a solution or dispersion of a hydrocolloid and optionally other matrix components;

adding to said solution or dispersion said at least one fat-soluble active substance, optionally dissolved in a solvent;

homogenising the mixture thus obtained, e.g. in a rotor stator, to prepare a solution or dispersion of said at least one active substance in a matrix;

finely dividing and drying, e.g. spray drying, the mixture thus obtained, optionally in the presence of a coating materials such as starch, to prepare a mass of particles each containing said at least one active substance embedded in said matrix.

The invention also relates to a unit dosage form comprising a composition according to the invention wherein the content of said active substance is from 10 to 500 microg and the content of said at least one dietary mineral is at least 10% of the total weight of the dosage form.

The invention also relates to a process for preparing a unit dosage form in the form of a tablet, which process comprises the steps of blending of microcapsules comprising at least one fat-soluble active substance selected from a vitamin K compound or a provitamin or a prodrug of a vitamin K compound embedded in a matrix comprising a hydrocolloid and optionally one or more other matrix components in an amount of from 10 to 500 µg with at least 10% by weight of the total weight of the dosage form of at least one dietary mineral and compressing the resulting blend to form a tablet.

The invention further relates to a microcapsule comprising at least one fat-soluble active substance selected from a vitamin K compound or a provitamin or prodrug of a vitamin K compound, optionally dispersed in an additional oil for dissolving of the active substance(s), and embedded in a matrix comprising a hydrocolloid and optionally one or more other matrix components, wherein the content of fat-soluble active substance is from 0.01 to 15 wt %, and the total content of active substance(s) and additional oil is from 0.01 to 15% of total weight of the microcapsule.

Vitamin K in the sense of the invention shall be understood as Vitamin K1, Vitamin K2 or a provitamin or prodrug of vitamin K or combinations thereof.

The invention also relates to a process of preparing a microcapsule according to the invention, which process comprises the steps of
  providing a solution or dispersion of said hydrocolloid and said optionally other matrix components,
  adding to said solution or dispersion said at least one fat-soluble active substance
  treating the mixture thus obtained to prepare a solution or dispersion of said at least one active substance in said matrix
  finely dividing and drying the mixture thus obtained to prepare a mass of particles each containing said at least one active substance embedded in said matrix.

Finally, the invention relates to products comprising the composition or microcapsule of the invention, uses thereof and a method of treatment of a condition associated with vitamin K deficiencies.

It has surprisingly been found that a more stable formulation of vitamin K (K1 and/or K2) compounds or provitamins or prodrugs of vitamin K compounds together with dietary minerals can be obtained by the use of the vitamin K comprised in microcapsules according to the invention. The overall stability of the vitamin K can be markedly improved if the vitamins are formulated as microcapsules before mixing with the dietary minerals followed by formulation of the mixture in a conventional dosage form such as a tablet.

Also the microcapsules themselves comprising the vitamin K compounds are protected against moisture and remain free-flowing during storage even under tropical conditions. They have high stability both as a vitamin K formulation and when formulated in a multimineral formulation.

Moreover, the resulting composition is easy to handle and stable during processing and has good storage properties over time of the final application/dosage form, such as the tablet. During finished product manufacturing it is important that the product has good "flow" properties to minimise losses. The product should be a homogenous blended product, and be resistant to pressure and temperature during the tableting process.

After testing and analysis of a large number of potential carriers and coatings the present invention has revealed that only microcapsules comprising the vitamin K compound could result in a stable product under the given conditions.

In particular, it has also been found that vitamin K1 and K2 formulated as microcapsules can be combined with calcium salts, magnesium salts and other important metal salts without the degradation issue associated with, for example, MK-7 combined with Ca or Mg directly. The combination does not degrade as rapidly as a combination with a conventional vitamin K1 or K2 product during processing and tableting (e.g. direct compression) and the K vitamin is more stable to light and air meaning it can be used in applications where light and air exposure are common and has a better storage stability such as in tablets.

The inventors also envisage extending the microencapsulation process to analogues of vitamin K1 and K2, called provitamins or prodrugs herein. The combination of a provitamin or prodrug which converts to the actual vitamin in vivo and the technology described herein therefore forms a further aspect of the invention.

The term "microcapsules" (or "beadlets") as used herein means particles each comprising a matrix material having embedded therein a plurality of solid or liquid micro particles or solute molecules. Microcapsules usually have a mean diameter of about 5 mm or smaller, e.g. between 1 mm and 0.05 mm, such as between 0.6 and 0.1 mm. They can also have a diameter e.g. between 2 mm and 0.01 mm, such as between 1.5 mm and 0.05, more particular between 1.0 and 0.2 mm, e.g. 0.1 to 0.2 mm.

The term "dispersion" as used herein covers both an emulsion meaning a mixture comprising liquid particles (e.g. oil droplets) dispersed in a liquid medium, e.g. water/aqueous solution, or a suspension meaning solid particles dispersed in a liquid medium, e.g. oil, water/aqueous solution.

DETAILED DESCRIPTION OF THE INVENTION

In one embodiment of the composition of the invention the at least one fat-soluble active substance is selected from vitamin K1, vitamin K2 and provitamins and prodrugs of vitamin K1 or vitamin K2, such as MK-6, MK-7 or MK-8, in particular K1 and MK-7, or a mixture thereof.

In another embodiment the content of said active substance(s) is from 0.01 to 15%, such as 0.1 to 10%, e.g. 0.2 to 5% or 0.5 to 3% or 1 to 2%, of the total weight of the microcapsules.

In one embodiment of the composition of the invention the at least one dietary mineral is selected from a salt of Li, Na, Mg, K, Ca, V, Cr, Mn, Fe, Co, Ni, Cu, Zn, Mo or Se, preferably Ca and/or Mg.

In another embodiment the at least one dietary mineral salt is any pharmaceutically acceptable salt, such as a halide, oxide, nitrate, stearate, sulphate, carbonate, glycerophosphate, hydrogen carbonate, dihydro- or anhydro-phosphate, e.g. a calcium salt, such as calcium carbonate, or a magnesium salt, such as magnesium oxide.

In one of such embodiments the composition comprises microcapsules comprising vitamin K2 in the MK-7 form as the at least one active substance and calcium carbonate or magnesium oxide as one of the at least one dietary mineral.

In another of such embodiments the composition comprises microcapsules comprising vitamin K1 as the at least one active substance and calcium carbonate or magnesium oxide as one of the at least one dietary mineral.

In yet another embodiment the content of said microcapsules is from 0.001 to 15%, such as 0.01 to 10%, e.g. 0.1 to 6%, of the total weight of the composition.

The content of said at least one dietary mineral may e.g. be at least 10% of the total weight of the composition, such as at least 20% or even at least 30%.

The composition of the invention may further comprise one or more additional active substances selected from vitamin E or E-acetate, vitamin A, D2 or D3, a monounsaturated or polyunsaturated fatty acid or a PUFA oil comprising mono-, di- and/or triglycerides of linoleic acid, linolenic acid, arachidonic acid, eicosapentaenoic acid and/or docosahexaenoic acid in combination with other fatty acids or the free fatty acids itself, β-carotene, zeaxanthin, lycopene, lutein or Q10, such as vitamin E or E-acetate, vitamin A, D2 or D3, a monounsaturated or PUFA oil, β-carotene, lycopene, lutein or Q10.

In one embodiment of the unit dosage form of the invention is a daily unit dosage form.

In one embodiment of the microcapsule of the invention the at least one fat-soluble active substance is selected from vitamin K1, vitamin K2 and provitamins and prodrugs of vitamin K1 or vitamin K2.

In another embodiment the content of the active substance(s) is 0.1 to 10%, e.g. 0.2 to 5% or 0.5 to 3% or 1 to 2%, of the total weight of the microcapsules.

In another embodiment the microcapsules comprising at least one fat-soluble active substance selected from a vitamin K compound or a provitamin or a prodrug of a vitamin K compound and comprised in the composition of the invention is obtained by a process according to the invention.

In a third embodiment the microcapsule of the invention is for use in a composition according to the invention.

The additional oil for solution of the active substance(s) is a conventional oil, such as a medium chained triglyceride, any vegetable edible oil, soy bean oil, olive oil, palm oil, sunflower oil, etc.

The fat-soluble active substances comprised in the microcapsule according to the invention or the microcapsule included in the composition according to the invention may be any substance selected from vitamin K1, vitamin K2 and provitamins or prodrugs of vitamin K1 or vitamin K2, viz. any substance of the vitamin K type which during storage, transport, handling and use requires protection, e.g. from oxygen, moisture, light radiation, and physical influences, in order to avoid physical and chemical decomposition of the substance. These active substances are further defined as being active in either a chemical or biological system. A provitamin, or a prodrug, of vitamin K will in vivo convert to the active vitamin and may be selected from any one of the substances disclosed in WO2010/035000 or WO2013/128037. These publications, which are referred to as a whole also disclose processes for manufacture of vitamin K compounds.

In one embodiment the microcapsule is made from a crystalline form of the actual vitamin K2 compound. In another embodiment the microcapsule is made from the oil of the actual vitamin K1 compound. In further another embodiment the microcapsule is made of crystalline form of the actual vitamin K1 and K2 alone or in combination with other vitamins, carotenoids or monounsaturated or polyunsaturated fatty acids.

The matrix hydrocolloid used according to the invention may be any hydrocolloid with emulsifying properties, such as an gum acacia, a protein, e.g. caseinate, whey protein, milk protein or hydrolysates, naturally occurring and modified polysaccharides and naturally occurring hydrocolloids, e.g. alginate, carrageenan, gelatine, gum ghatti, xanthan gum, gellan gum, modified gum acacia, carboxy methyl cellulose, pectins, modified pectins or mixtures. Starch derived from a natural source, such as potato, wheat, maize, tapioca, barley and rice, and modified starch are other examples of suitable matrix hydrocolloids, e.g. sodium octenyl succinate modified starch. The amount may e.g. make up from 15 to 80% by weight of the microcapsule, such as from 20 to 70% or from 25 to 60%.

The matrix can optionally comprise further components, such as dissolved carbohydrates, e.g. fructose, glucose, glucose syrup, high fructose corn syrup, sorbitol and sucrose or combinations thereof, and/or an antioxidant. The use of sorbitol and sucrose and/or an antioxidant is therefore an option. The use of the combination of a hydrocolloid and a carbohydrate is especially preferred.

The microcapsule may further contain conventional additives such as antioxidants, e.g. t-butylhydroxytoluene (BHT), t-butylhydroxyanisole (BHA), ascorbic acid, ascorbyl palmitate, sodium ascorbate, citric acid, sodium citrate, EDTA or its salts, tocopherols, TBHQ, ethoxyquine, propyl gallate, and extracts from herbs, i.a. rosemary or oregano extract; anti-caking agents, e.g. tri-calcium phosphate and silicates, i.a. silicon dioxide and sodium aluminium silicate; plasticizers, e.g. carbohydrates and carbohydrate alcohols, examples of which are saccharose, glucose, fructose, lactose, invert sugar, sorbitol, mannitol, Trehalose, Tagatose, Pullulan, Raftilose (oligofructose), dextrin, maltodextrin, glycerin, and mixtures thereof, such as saccharose, Trehalose, Pullulan, dextrin and Raftilose and mixtures thereof, emulsifiers and surfactants, e.g. ascorbyl palmitate, sucrose esters, mono- and diglycerides of fatty acids and derivatives thereof, and lecithin.

The microencapsulation process typically involves dissolution of the fat-soluble active ingredient in an oil such as MCT oil. The hydrocolloid is then dissolved in a solvent such as water, optionally together with other excipients such as sugar. The two phases are then mixed and homogenised in a homogeniser such as a rotor stator. The homogeniser composition may then be sprayed. In order to facilitate spraying, it may be necessary to dilute the homogenised mixture.

The homogenised mixture is then preferably spray dried, but also other methods of drying can be used. The dividing and drying of the solution or dispersion to produce a mass of particles can be done in any conventional way, such as spray cooling, spray drying or sheet drying and crushing, see e.g. WO 91/06292.

In one embodiment of the process of the invention a powdering agent, such as native corn starch, is fed to the microcapsules during the finely dividing and drying step.

In another embodiment of the process a further step of treatment of the solution or dispersion in a high pressure homogenisator is included, such as treatment in a Niro Soavi High Pressure Homogenisator or Rannie.

In one embodiment the product of the invention is a food, a food supplement, a beverage, a pharmaceutical or veterinary product, a feed or feed supplement, a personal care product or a household product, such as a nutraceutical or pharmaceutical product for oral administration.

For instance a sucrose product can be fortified with the composition of the invention.

The product may for instance be for use in the treatment of a condition associated with vitamin K deficiencies, such as for the treatment of osteoporosis and conditions of the cardiovascular system such as arteriosclerosis or in assisting blood clotting.

In one embodiment the invention relates to use of the composition of the invention for the manufacture of tablets containing the active substance selected from vitamin K products.

The composition of the invention may also be used in a method of treatment of a condition associated with vitamin K deficiencies comprising administering to a patient in need thereof an effective amount of a composition according to the invention.

The process of the invention may be carried out in accordance with the following general recipe or as shown in the examples.

The water soluble ingredients, including some of the matrix components, are added to water, optionally at elevated temperature, and dissolved under agitation. The fat-soluble ingredients are mixed and then added to the aqueous phase and the mixture is homogenised in a rotor/stator dissolver to prepare a solution or dispersion. The solution or dispersion is diluted, if necessary, to an appropriate viscosity before the solution or dispersion is finely divided and dried by a conventional method. If applicable a powdering agent is added during the diving and drying.

If applicable the solution or dispersion is subjected to an additional treatment in a high pressure homogenisator.

The composition of the invention is suitable for use in the treatment of a condition associated with vitamin K1 or K2 such as for the treatment of osteoporosis and conditions of the cardiovascular system such as arteriosclerosis or in assisting blood clotting.

The composition of the invention is also suitable for use in a method of treating a condition associated with vitamin K1 or K2 comprising administering to a patient in need thereof an effective amount of a composition of the invention.

Whilst the invention has been described in relation to vitamin K, the microencapsulation techniques described herein could be applied to other vitamins and other compounds that are readily degraded during their storage, such as polyunsaturated fatty acids and derivatives thereof, such as omega-3s. Vitamins that could be microencapsulated include vitamin A, vitamins of the B family and vitamin D family of vitamins. The microencapsuled compounds might be used in conjunction with a dietary mineral but can equally be used per se.

Viewed from a further aspect therefore the invention provides a composition comprising A) microcapsules comprising at least one fat-soluble active substance which degrades on storage, such as a vitamin or a provitamin or a prodrug of a vitamin or a polyunsaturated fatty acid or derivative thereof, embedded in a matrix comprising a hydrocolloid and optionally one or more other matrix components, and B) at least one dietary mineral.

The microcapsules of part A) above also form a further aspect of the invention.

Viewed from another aspect the invention provides a process of preparing a microcapsule which process comprises the steps of providing a solution or dispersion of a hydrocolloid and optionally other matrix components, adding to said solution or dispersion said at least one fat-soluble active substance which degrades on storage, such as a vitamin or a provitamin or a prodrug of a vitamin or a polyunsaturated fatty acid or derivative thereof;

treating the mixture thus obtained to prepare a solution or dispersion of said at least one active substance in said matrix finely dividing and drying the mixture thus obtained to prepare a mass of particles each containing said at least one active substance embedded in said matrix.

The invention will now be described in further detail with reference to the following examples.

EXAMPLES

Stability Testing of Tablets:

The compositions comprising vitamin K and dietary minerals are tested for stability at long term (25° C./60% RH) and accelerated conditions (40° C./75 30% RH). The vitamin K2, MK-7 compound was provided by Kappa Bioscience

Example 1

Preparations of Microcapsules Comprising Vitamin K

Microcapsules Comprising Vitamin K2 in an Amount of 0.2 wt % Crystalline MK-7

8.9 g Vitamin K2/MK-7 was dissolved in 60 g MCT (medium chain triglycerides) oil at a temperature of 62° C.

1250 g acacia gum and 1800 g sugar were dissolved in 2200 g water at 62° C. under agitation. The oil phase containing the MK-7 was added to the aqueous solution, and the solution was stirred below 65° C.

The dispersion was homogenized well in a rotor/stator; alternatively a high pressure homogenizer can be applied; and diluted to a sprayable viscosity.

Subsequently, the dispersion was finally divided in a spray drying tower, where the dispersion particles were covered with a thin layer of starch and dried.

The mean droplet size (d0.5, measured by a Master sizer, Malvern instruments) in the final microcapsules was 100-800 nm, the content of MK-7 was 0.2 wt %, the residual water content was 3-5 wt %, and the bulk density, loose/tapped was 0.71/0.86 g/ml.

Comparative Example 1

A Vitamin K2 MK-7 in MCC (microcrystalline cellulose) powder was used.

Example 2

Compositions According to the Invention Containing MgO as Dietary Mineral and Microcapsules Comprising Crystalline MK-7

16 g microencapsulated Vitamin K2 (0.2 wt % MK7, example 1) was mixed with 274 g MgO (Magnesia 82600), 274 g microcrystalline cellulose powder (MCC) and 5 g magnesium stearate to a homogenous mixture. This mixture was used to produce tablets.

Comparative Example 2

Compositions Containing MgO as Dietary Mineral and MK-7 in MCC Powder 45 g Vitamin K2, MK7 in MCC powder (0.2%, Kappa Biosceince, comparative example 1) was blended together with 373.5 g MgO (Magnesia 82600), 373.5 g MCC powder and 8 g magnesium stearate to a homogenous mixture. This mixture was used to produce tablets.

Tablet Parameters:

Tablet machine: Killian T 300

Tablet size: 11 mm

Tablet pressure: 39 kN

Stability Testing of Tablets

Stability testing at long term (25° C./60% RH) and accelerated conditions (40° C./75% RH) for tablets containing microcapsules comprising MK7 and MgO (example 2) and compared with tablets containing MK7 in MCC (non-coated) and MgO (comparative example 2) have been carried out. Table 1 below shows the stability results (% w/w):

TABLE 1

| Temperature | Amount of MK-7 recovered after storage (% w/w) | | | | |
|---|---|---|---|---|---|
| | 25° C. | | 40° C. | | |
| Time | Initial | 1 month | 3 month | 1 month | 3 month |
| Microcapsules of MK-7 (0.2%) with MgO | 100 | 100 | 98 | 96 | 90 |
| MK7 (0.2%) in MCC powder with MgO | 100 | 19 | 8 | 7 | 3 |

Example 3

Compositions According to the Invention Containing $CaCO_3$ as Dietary Mineral and Microcapsules Comprising Crystalline MK-7

16 g microencapsulated Vitamin K2 (0.2% MK7, example 1) was mixed with 459 g $CaCO_3$ (Presscal 90%), 90 g microcrystalline cellulose powder (MCC) and 5 g magnesium stearate to a homogenous mixture. This mixture was used to produce tablets.

Comparative Example 3

Compositions containing $CaCO_3$ as dietary mineral and MK-7 in MCC powder 45 g Vitamin K2 MK7 in MCC powder (0.2%, Kappa Biosceince, comparative 15 example 1) was mixed with 645 g $CaCO_3$ (Presscal 90%), 102 g MCC powder and 8 g magnesium stearate to a homogenous mixture. This mixture was used to produce tablets.

Tablet Parameters:
Tablet machine: Killian T 300
Tablet size: 11 mm
Tablet pressure: 39 kN
Stability Testing of Tablets
Stability testing at long term (25° C./60% RH) and accelerated conditions (40° C./75% RH) for tablets containing microcapsules comprising MK7 and $CaCO_3$ (example 3) and compared with MK7 in MCC (non-coated) and $CaCO_3$ (comparative example 3) has been carried out. Table 2 below shows the stability results (% w/w):

TABLE 2

| Temperature | Amount of MK-7 recovered after storage (% w/w) | | | | |
|---|---|---|---|---|---|
| | 25° C. | | 40° C. | | |
| Time | Initial | 1 month | 3 month | 1 month | 3 month |
| Microencapsulated MK-7 (0.2%) with CaCO3 | 100 | 100 | 99 | 99 | 95 |
| MK7 (0.2%) in MCC powder with CaCO3 | 100 | 89 | 85 | 76 | 60 |

Example 4

Microcapsules Comprising Vitamin K1 in an Amount of 1.0% by Weight 7.5 g Vitamin K1 is weighed in at a temperature of 65° C.
176 g acacia gum and 476 g spray dried glucose syrup are dissolved in 490 g water at 65° C. under agitation. The oil phase containing the vitamin K1 is added to the aqueous solution and stirred below 70° C.

The dispersion is homogenized well in a rotor/stator; alternatively a high pressure homogenizer can be applied; and diluted to a sprayable viscosity.

Subsequently, the dispersion is finally divided in a spray drying tower, where 20 the dispersion particles are covered with a thin layer of starch and dried.

The content of MK-7 is 1.0% by weight, and the residual water content 2-3%.

Comparative Example 4

A conventional spray-dried Vitamin K1 product, containing 1.0% K1 is used.

Example 5

Compositions According to the Invention Containing MgO as Dietary Mineral and Microcapsules Comprising Vitamin K1

10 g microencapsulated Vitamin K1 (1.0%, example 4) is mixed with 274 g MgO (Magnesia 82600), 274 g microcrystalline cellulose powder (MCC) and 5 g magnesium stearate to a homogenous mixture. This mixture is used to produce tablets.

Comparative Example 5

Compositions Containing MgO as Dietary Mineral and Conventional Spray-Dried Vitamin K1 Product 10 g spray dried Vitamin K1 (1.0%, comparative example 4) is mixed with 20 274 g MgO, 274 g microcrystalline cellulose powder (MCC) and 5 g magnesium stearate to a homogenous mixture. This mixture is used to produce tablets.

Tablet Parameters:
Tablet machine: Killian T 300
Tablet size: 11 mm
Tablet pressure: 39 kN
Stability Testing of Tablets
Stability testing at long term (25° C./60% RH) and accelerated conditions (40° C./75% RH) for tablets containing microcapsules comprising vitamin K1 and MgO (example 5) and spray dried vitamin K1 and MgO (comparative example 5) are on-going.

Example 6

Compositions According to the Invention Containing CaCO3 as Dietary Mineral and Microcapsules Comprising Vitamin K1

10 g microencapsulated Vitamin K1 (1.0% K1, example 4) is mixed with 858 g CaCO3 (Calci-Press 95MD) 30 g Kollidon CL-F (BASF) and 8.4 g magnesium stearate to a homogenous mixture. This mixture is used to produce tablets.

Comparative Example 6

Compositions Containing CaCO3 as Dietary Mineral and Conventional Spray-Dried Vitamin K1 Product 10 g vitamin K1 (comparative example 5) is mixed with 858 g CaCO3 (Calci-15 Press 95MD) 30 g Kollidon CL-F (BASF) and 8.4 g magnesium stearate to a homogenous mixture. This mixture is used to produce tablets.

Tablet Parameters:
Tablet machine: Korsch PH 106 20
Tablet size: Oblong Calcium

Tablet pressure: 20 kN
Stability Testing of Tablets
Stability testing at long term (25° C./60% RH) and accelerated conditions (40° C./75% RH) for tablets containing microcapsules comprising vitamin K1 and CaCO3 (example 6) and spray dried vitamin K1 and CaCO3 (comparative example 6) are on-going.

Example 7

Further stability testing has been carried out on the compositions of examples 2 and 3 and comparative compositions 2 and 3, this time for 12 months.
Material
Example 1 microcapsules and MgO, powder and tablets AGF4
Example 1 microcapsules and CaCO$_3$, powder and tablets AGF5
Vitamin K2 in MCC (Comp Example 1) and MgO, powder and tablets
Vitamin K2 in MCC (Comp Example 1) and CaCO$_3$, powder and tablets
The tablets were produced as described in example 2. They were either used as such or ground in a mortar to obtain powder.
HPLC Conditions:
The samples were analysed by reversed phase HPLC (method ID MK-7 short).
MK-7 was quantified using external standard calibration and UV detection at 270 nm.
A detector with 60 mm flow celle was used, due to low concentration samples.
Results
The results for Example 2 and 3 products and comparative example 2 and 3 are presented in Table 3 and Table 4, respectively.

TABLE 3

Stability results for Example 2 powder and tablets

|  | T = 0 | T = 1 month | | T = 3 months | | T = 12 months | |
| --- | --- | --- | --- | --- | --- | --- | --- |
|  |  | 25° C. | 40° C. | 25° C. | 40° C. | 25° C. | 40° C. |
| Powder AGF4 with MgO | 71 | 65 | 62 | 69 | 65 | 67 | 57 |
| Tablets AGF4 with MgO | 66 | 68 | 63 | 65 | 59 | 61 | 53 |
| Powder AGF5 with CaCO3 | 76 | 64 | 72 | 77 | 75 | 77 | 71 |
| Tablets AGF5 with CaCO3 | 69 | 70 | 68 | 68 | 65 | 66 | 59 |

TABLE 4

| T = | T = 1 month | | T = 3 months | | T = 12 months | |
| --- | --- | --- | --- | --- | --- | --- |
| 0 | 25° C. | 40° C. | 25° C. | 40° C. | 25° C. | 40° C. |
| Tablets MCC with MgO | 99 | 19 | 7.4 | 8.4 | 2.9 | 1.3 | 0.7 |
| Tablets MCC with CaCO3 | 104 | 88 | 84 | 75 | 60 | 62 | 30 |

SUMMARY

The results from the stability testing of MK-7 in powder and tablets with CaCO$_3$ and MgO show that the formulations of the invention are more stable than the corresponding MCC formulations with respect to MK-7 content.

For the ground powder and tablets with MgO and CaCO$_3$ only small changes in the result for the MK-7 content is observed during the 12 months testing period, for material stored at 25° C. For material stored at 40° C. the content of MK-7 decreases slightly.

The results for the MCC products with MgO and CaCO$_3$ show a significant decrease in the amount of MK-7, especially for the material containing MgO. At the 1 months testing time point the amount of MK-7 is reduced to less than 20% of the T=0 results for the tablets with MCC powder and MgO.

For tablets with MCC powder and CaCO$_3$ the one month results are better than for MgO, however compared to the products of the invention the reduction of MK-7 is significant.

The comparative study of the effect of MgO and CaCO$_3$ on MK-7 shows that the stability of MK-7 is significantly improved in the microcapsule formulation.

The invention claimed is:
1. A composition comprising:
A) a first component being microcapsules consisting of at least one fat-soluble active substance selected from a vitamin K compound or a provitamin or a prodrug of a vitamin K compound embedded in a matrix comprising a hydrocolloid and optionally one or more other matrix components; and
B) a separate second component being at least one dietary mineral, wherein the dietary mineral is selected from a calcium salt, a magnesium salt, calcium carbonate or magnesium oxide.
2. The composition according to claim 1, wherein said at least one fat-soluble active substance is vitamin K1, vitamin K2, provitamins and prodrugs of vitamin K1 or vitamin K2, MK-6, MK-7, MK-8, or a mixture thereof.
3. The composition according to claim 1, wherein the content of said active substance is from 0.01 to 15%, 0.1 to 10%, 0.2 to 5%, or 1 to 3% of the total weight of the microcapsules.
4. The composition according to claim 1, wherein the content of said microcapsules is from 0.001 to 15%, 0.01 to 10%, or 0.1 to 6% of the total weight of the composition.
5. The composition according to claim 1, wherein the content of said at least one dietary mineral is at least 10%, at least 20%, or at least 30% of the total weight of the composition.
6. The composition according to claim 1, further comprising one or more additional active substances selected from the group consisting of vitamin D2, vitamin D3, vitamin E, vitamin E-acetate, vitamin A, a monounsaturated fatty acid, a polyunsaturated fatty acid (PUFA), a PUFA oil, β-carotene, zeaxanthin, lycopene, lutein and Q10.

7. The composition according to claim 1, wherein said microcapsules comprise vitamin K2 in the MK-7 form as the at least one fat-soluble active substance, and wherein said at least one dietary mineral is calcium carbonate or magnesium oxide.

8. The composition according to claim 1, wherein said microcapsules comprise vitamin K1 as the at least one fat-soluble active substance, and wherein said at least one dietary mineral is calcium carbonate or magnesium oxide.

9. A unit dosage form comprising the composition according to claim 1, wherein the content of said active substance is from 10 to 500 µg, 25 to 250 µg, or 50 to 200 µg, and wherein the content of said at least one dietary mineral is at least 10%, at least 20%, or at least 30% of the total weight of the dosage form.

10. The unit dosage form according to claim 9 which is a daily unit dosage form.

11. A process for preparing the unit dosage form according to claim 9 in the form of a tablet, comprising:
 a) blending microcapsules comprising at least one fat-soluble active substance selected from a vitamin K compound or a provitamin or a prodrug of a vitamin K compound embedded in a matrix comprising a hydrocolloid and optionally one or more other matrix components in an amount of from 10 to 500 µg with at least 10% by weight of the total weight of the dosage form of at least dietary mineral; and
 b) compressing the resulting blend to form a tablet.

12. The composition according to claim 1, wherein said hydrocolloid is an acacia gum, a protein or a starch.

13. The composition according to claim 1, wherein said matrix further contains antioxidants and/or carbohydrates.

14. A product comprising the composition according to claim 1.

15. The product according to claim 14, which is a food, a food supplement, a beverage, a pharmaceutical or veterinary product, a feed or feed supplement, a personal care product, or a household product.

16. The product according to claim 14, which is a nutraceutical or pharmaceutical product for oral administration.

17. The product according to claim 14 for use:
 a) in the treatment of a condition associated with vitamin K deficiencies;
 b) in the treatment of osteoporosis;
 c) in the treatment of conditions of the cardiovascular system;
 d) in the treatment of arteriosclerosis; or
 e) in assisting blood clotting.

18. A method of treating a condition associated with vitamin K1 or K2, comprising administering to a patient in need thereof an effective amount of the composition according to claim 1.

* * * * *